(12) United States Patent
Lodi

(10) Patent No.: US 7,530,977 B2
(45) Date of Patent: May 12, 2009

(54) INFUSION AND/OR WITHDRAWAL FITTING FOR BIOMEDICAL FLUID CIRCUITS

(75) Inventor: Marco Lodi, Mirandola (IT)

(73) Assignee: Sherwood Services AG, Schaffhausen (CH)

( * ) Notice: Subject to any disclaimer, the term of this patent is extended or adjusted under 35 U.S.C. 154(b) by 220 days.

(21) Appl. No.: 11/466,692

(22) Filed: Aug. 23, 2006

(65) Prior Publication Data

US 2007/0060912 A1    Mar. 15, 2007

Related U.S. Application Data

(63) Continuation of application No. PCT/IT2004/000079, filed on Feb. 23, 2004.

(51) Int. Cl.
*A61M 39/00* (2006.01)
(52) U.S. Cl. ...................................... 604/533
(58) Field of Classification Search ......... 604/533–539, 604/905; 215/216, 235–237
See application file for complete search history.

(56) References Cited

U.S. PATENT DOCUMENTS

| 4,963,132 | A | 10/1990 | Gibson ..................... 604/256 |
| 5,413,561 | A | 5/1995 | Fischell et al. ............. 604/167 |
| 6,036,672 | A | 3/2000 | Allen et al. ................. 604/167 |
| 6,394,983 | B1 | 5/2002 | Mayoral et al. ............ 604/192 |
| 2004/0168690 | A1* | 9/2004 | Payne ..................... 128/207.14 |

FOREIGN PATENT DOCUMENTS

| DE | 20021431 U1 | 4/2001 |
| DE | 20203154 U1 | 6/2002 |
| WO | WO 2005079907 A1 * | 9/2005 |

OTHER PUBLICATIONS

International Search Report (with Written Opinion), PCT/IT2004/000079, 9 pages, Mailed Sep. 15, 2004.

* cited by examiner

*Primary Examiner*—Nicholas D Lucchesi
*Assistant Examiner*—Theodore J Stigell
(74) *Attorney, Agent, or Firm*—King & Spalding

(57) ABSTRACT

An infusion and/or withdrawal fitting for biomedical fluid circuits is defined by a tubular conduit having a first end connectable to a biomedical fluid circuit, and a second end which is closed by a plug having a collar connected to the plug at a weakened portion; the conduit having a breaking member for breaking the weakened portion when fitting the plug to the conduit, and for retaining the collar on the conduit.

19 Claims, 1 Drawing Sheet

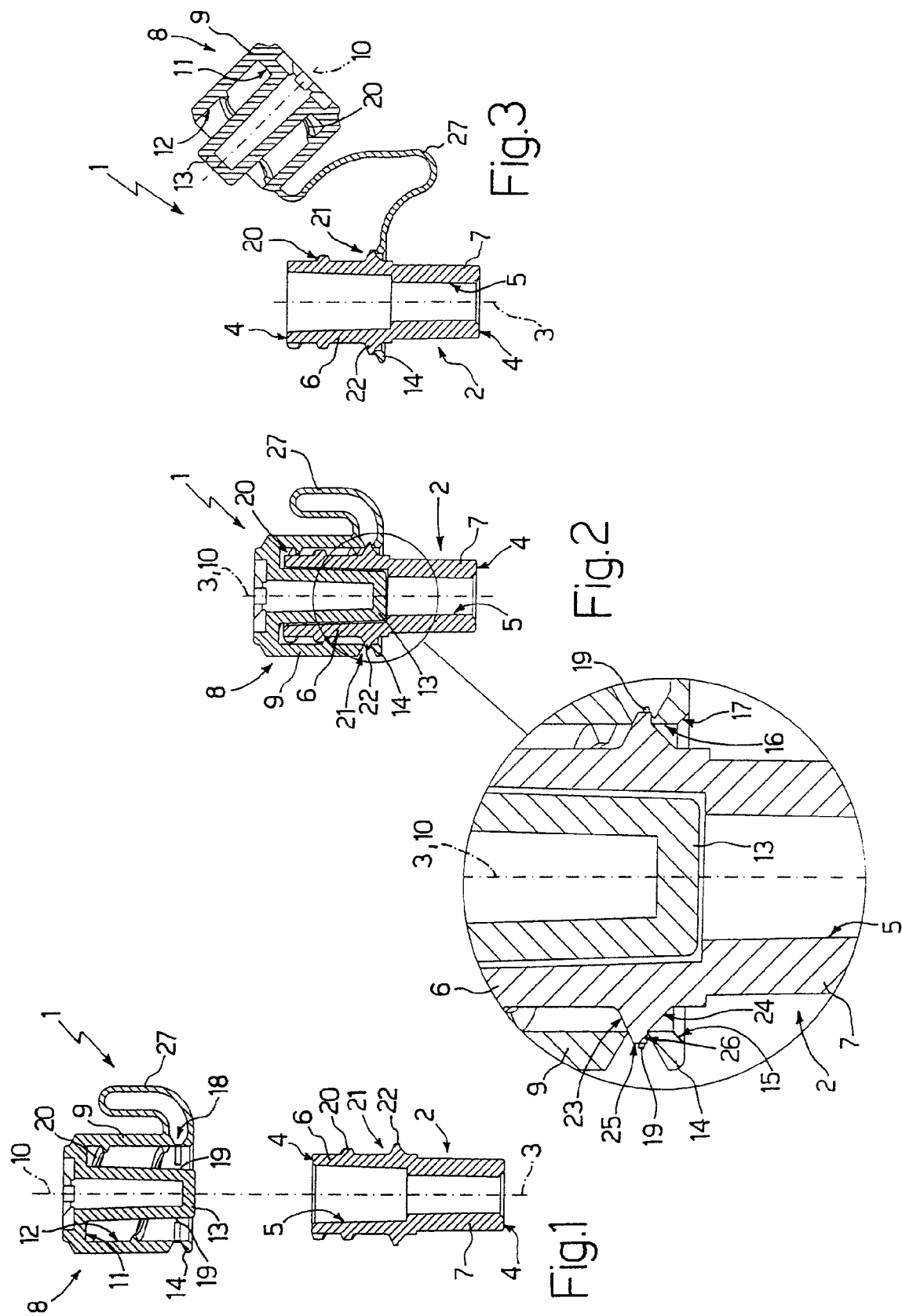

INFUSION AND/OR WITHDRAWAL FITTING FOR BIOMEDICAL FLUID CIRCUITS

CROSS-REFERENCE TO RELATED APPLICATION

This application is a continuation of co-pending International Application No. PCT/IT2004/000079 filed Feb. 23, 2004, which designates the United States.

TECHNICAL FIELD

The present invention relates to an infusion and/or withdrawal fitting for biomedical fluid circuits.

More specifically, the present invention relates to an infusion and/or withdrawal fitting for biomedical fluid circuits, of the type comprising a tubular conduit having a first end connectable to a biomedical fluid circuit, and a second end closed by a cap.

BACKGROUND

The cap normally comprises a plug movable between an open position and a closed position for opening and closing the second end respectively; and an elastically deformable collar fitted to the conduit and connected to the plug by a flexible element to keep the plug and collar connected to each other when the plug is in the open position.

Known infusion and/or withdrawal fittings of the type described above have several drawbacks, mainly due to assembly of the collar to the conduit being relatively complicated, by requiring elastic deformation of the collar by the user.

A further drawback of known infusion and/or withdrawal fittings of the type described above lies in the relative ease with which the collar works loose from the conduit.

SUMMARY

It is an object of the present invention to provide an infusion and/or withdrawal fitting for biomedical fluid circuits, designed to eliminate the aforementioned drawbacks.

According to the present invention, there is provided an infusion and/or withdrawal fitting for biomedical fluid circuits. The fitting comprising a tubular conduit having first and second ends, and a cap. The first end connectable to a biomedical fluid circuit. The cap is adapted for fitting onto said second end. The cap comprises a plug, a collar, and a connecting means. The plug is movable between an open position and a closed position for opening and closing the second end. The connecting means adapted for keeping the plug connected to the collar when the plug is in an open position. The cap comprises a weakened portion connecting the plug to the collar. And the conduit comprises means for breaking the weakened portion when fitting the cap to the second end for detachment of the plug from the collar and for retaining the collar on the conduit.

According to the present invention, there is provided a fitting for biomedical fluid circuits. The fitting comprises a tubular conduit having first and second ends, and a cap. The first end adapted for connection to a circuit. The cap is adapted to fit on the second end of the conduit. The cap comprises a plug movable between open and closed positions, a collar, and a flexible element interposed between the plug and the collar. The flexible element is adapted for keeping the plug connected to the collar. The cap also includes a weakened portion for connecting the plug to the collar. The conduit includes an annular flange projecting outwards from an outer surface of the conduit. The flange is adapted to break the weakened portion when fitting the cap to the second end, e.g., to detach the plug from the collar and for retaining the collar on the conduit.

BRIEF DESCRIPTION OF THE DRAWINGS

A non-limiting embodiment of the present invention will be described by way of example with reference to the accompanying drawings, in which:

FIGS. 1, 2, and 3 show longitudinal sections, with parts enlarged for clarity, of a preferred embodiment of the infusion and/or withdrawal fitting according to the present invention in different operating positions.

DETAILED DESCRIPTION

Number 1 in FIG. 1 indicates as a whole an infusion and/or withdrawal fitting for biomedical fluid circuits (not shown).

Fitting 1 comprises a tubular conduit 2, which has a given longitudinal axis 3, is defined axially by two surfaces 4 substantially perpendicular to axis 3, is defined internally by a substantially truncated-cone-shaped surface 5, and in turn comprises a wide, substantially cylindrical top portion 6, and a narrow, substantially truncated-cone-shaped bottom portion 7 connectable to a biomedical fluid circuit (not shown).

Portion 6 is closed by a cap 8 comprising a plug 9, which has a given longitudinal axis 10, is substantially cup-shaped, is defined internally by an annular end wall 11 substantially perpendicular to axis 10, and by a substantially cylindrical lateral wall 12, and is closed axially, at wall 11, by a central shank 13, which projects axially from wall 11, is substantially in the form of a truncated-cone-shaped cup with the same taper as surface 5, and has a concavity opposite the concavity of plug 9.

Plug 9 also has an annular collar 14, which is substantially coaxial with axis 10, is defined internally by a lateral wall 15 comprising a cylindrical portion 16 coplanar with wall 12, and a truncated-cone-shaped portion 17, and is joined to plug 9 at a pre-cut weakened portion 18 defined by a number of teeth 19 substantially parallel to and equally spaced about axis 10.

Portion 6 and plug 9 are connectable by means of a threaded coupling 20, and with shank 13 engaging portion 6 (FIG. 2).

As shown in FIG. 2, when screwing cap 8 to portion 6, teeth 19 of weakened portion 18 are broken by a breaking device 21 comprising an annular flange 22 extending outwards from the outer surface of portion 6.

Flange 22 tapers outwards and is defined by two facing, substantially truncated-cone-shaped surfaces 23 and 24, which are connected to each other by a substantially cylindrical surface 25 coaxial with axis 3 and connected to surface 23, and by an annular surface 26 located between surfaces 24 and 25 and perpendicular to surface 25.

With reference to FIGS. 2 and 3, once teeth 19 are broken, flange 22 is located between plug 9 and collar 14 to retain collar 14 on conduit 2, collar 14 is connected in rotary manner to conduit 2, and plug 9 is movable between an open position and a closed position opening and closing portion 6 respectively.

In the open position opening portion 6, plug 9 is kept joined to collar 14 by a flexible element 27 extending between plug 9 and collar 14 and formed in one piece with plug 9 and collar 14.

I claim:

1. An infusion and/or withdrawal fitting for biomedical fluid circuits, the fitting comprising:
   a tubular conduit having a first end and a second end, the first end connectable to a biomedical fluid circuit; and
   a cap adapted to fit onto the second end of the tubular conduit, the cap comprising:
      a plug movable between an open position and a closed position for opening and closing the second end of the tubular conduit;
      a collar;
      a connector adapted for keeping the plug connected to the collar when the plug is in the open position; and
      a weakened cap portion between the plug and the collar;
   wherein the tubular conduit comprises a protrusion that breaks the weakened cap portion upon fitting of the cap to the second end of the tubular conduit such that the plug detaches from the collar at the weakened cap portion but remains connected to the collar by the connector, and the collar is retained on the tubular conduit.

2. A fitting as claimed in claim 1, wherein said protrusion that breaks the weakened cap portion of the cap upon installation of the cap to the second end of the tubular conduit comprises an annular flange projecting outwards from an outer surface of said conduit.

3. A fitting as claimed in claim 2, wherein said flange tapers outwards.

4. A fitting as claimed in claim 2, wherein said flange is defined by a substantially truncated-cone-shaped first surface, by a substantially truncated-cone-shaped second surface, and by a substantially cylindrical third surface located between said first and said second surfaces.

5. A fitting as claimed in claim 4, wherein said flange is also defined by an annular fourth surface located between said second surface and said third surface.

6. A fitting as claimed in claim 5, wherein said third surface and said fourth surface are substantially perpendicular to each other.

7. A fitting as claimed in claim 1, wherein the cap has a given longitudinal axis, and the weakened cap portion comprises a pre-cut portion having one or more teeth distributed about said axis and disposed between the collar and the plug.

8. A fitting as claimed in claim 1, wherein said connector comprises a flexible element interposed between said plug and said collar.

9. A fitting as claimed in claim 8, wherein the flexible element is formed in one piece with said plug and said collar.

10. A fitting as claimed in claim 1, further comprising a threaded portion for coupling said cap to said second end.

11. A fitting for biomedical fluid circuits, the fitting comprising:
    a tubular conduit having first and second ends, the first end adapted for connection to a circuit; and
    a cap adapted to couple with the second end of the conduit, the cap comprising:
       a plug movable between open and closed positions;
       a collar;
       a flexible element interposed between the plug and the collar, the flexible element adapted for keeping the plug connected to the collar; and
       a weakened cap portion between the plug and the Collar;
    wherein the conduit includes an annular flange projecting outwards from an outer surface of the conduit, the flange adapted to break the weakened cap portion when coupling the cap to the second end such that the plug detaches from the collar at the weakened cap portion but remains connected to the collar by the flexible element.

12. A fitting according to claim 11, wherein the flange is defined by a substantially truncated-cone-shaped first surface, a substantially truncated-cone-shaped second surface, and a substantially cylindrical third surface located between said first and said second surfaces.

13. A fitting according to claim 11, wherein the weakened cap portion between the plug and the collar comprises one or more teeth.

14. A fitting according to claim 11, wherein:
    the cap is configured to be screwed to couple with the second end of the conduit; and
    the flange of the conduit is adapted to break the weakened cap portion when the cap is screwed onto the second end of the conduit.

15. A fitting according to claim 11, wherein the flange restrains the collar to the second end of the conduit.

16. A fitting according to claim 11, wherein the plug, collar, and flexible element of the cap are formed in a single piece.

17. A fitting for a biomedical conduit, the fitting comprising:
    a tubular conduit for communicating biomedical fluid; and
    a cap adapted to attach to an end of the tubular conduit, the cap including:
       a collar;
       a plug movable between an open position and a closed position for opening and closing the end of the tubular conduit;
       a connector configured to maintain the plug connected to the collar when the plug is in an open position; and
       a breakable portion between the plug and the collar;
    wherein the breakable portion between the plug and the collar is configured to automatically break apart due to interaction with a flange on the tubular conduit during attachment of the cap to the end of the tubular conduit such that the collar is retained on the tubular conduit by the flange and the plug remains connected to the collar by the connector.

18. A fitting according to claim 17, wherein the breakable portion between the plug and the collar comprises one or more teeth.

19. A fitting according to claim 17, wherein:
    the cap is configured to be attached via screwing onto the end of the tubular conduit; and
    wherein the breakable portion between the plug and the collar is configured to automatically break apart upon screwing the cap to the tubular conduit.

* * * * *